(12) United States Patent
Reich et al.

(10) Patent No.: US 8,269,960 B2
(45) Date of Patent: Sep. 18, 2012

(54) COMPUTER-IMPLEMENTED METHODS FOR INSPECTING AND/OR CLASSIFYING A WAFER

(75) Inventors: Juergen Reich, Campbell, CA (US); Louis Vintro, Menlo Park, CA (US); Prasanna Dighe, Fremont, CA (US); Andrew Steinbach, Menlo Park, CA (US); Daniel Kavaldjiev, San Jose, CA (US); Stephen Biellak, Sunnyvale, CA (US)

(73) Assignee: KLA-Tencor Corp., San Jose, CA (US)

( * ) Notice: Subject to any disclaimer, the term of this patent is extended or adjusted under 35 U.S.C. 154(b) by 373 days.

(21) Appl. No.: 12/179,260

(22) Filed: Jul. 24, 2008

(65) Prior Publication Data

US 2010/0060888 A1    Mar. 11, 2010

(51) Int. Cl.
*G01N 21/00*    (2006.01)

(52) U.S. Cl. ............... 356/237.5; 356/237.1; 356/237.6; 700/110; 382/149

(58) Field of Classification Search .... 356/237.2–237.5; 700/110; 382/149; 702/40
See application file for complete search history.

(56) References Cited

U.S. PATENT DOCUMENTS

| | | | |
|---|---|---|---|
| 4,162,126 A | 7/1979 | Nakagawa et al. | |
| 4,410,278 A | 10/1983 | Makihira et al. | |
| 4,845,558 A | 7/1989 | Tsai et al. | |
| 4,898,471 A | 2/1990 | Vaught et al. | |
| 5,355,212 A * | 10/1994 | Wells et al. | 356/237.4 |
| 5,555,315 A | 9/1996 | Itakura | |
| 5,608,453 A | 3/1997 | Gerber et al. | |
| 5,625,451 A | 4/1997 | Schiff et al. | |
| 5,661,408 A | 8/1997 | Kamieniecki et al. | |
| 5,712,701 A | 1/1998 | Clementi et al. | |
| 5,903,342 A | 5/1999 | Yatsugake et al. | |
| 5,909,276 A | 6/1999 | Kinney et al. | |
| 5,991,699 A | 11/1999 | Kulkarni et al. | |
| 6,118,525 A | 9/2000 | Fossey et al. | |
| 6,171,975 B1 | 1/2001 | Hase et al. | |
| 6,201,601 B1 | 3/2001 | Vaez-Iravani et al. | |
| 6,265,719 B1 | 7/2001 | Yamazaki et al. | |

(Continued)

FOREIGN PATENT DOCUMENTS

JP    2000-002514    1/2000

(Continued)

OTHER PUBLICATIONS

U.S. Appl. No. 60/974,030 (Bhaskar et al.) entitled Systems and Methods for Creating Persistent Data for a Wafer and for Using Persistent Data for Inspection-Related Functions, filed Sep. 20, 2007.

(Continued)

*Primary Examiner* — Tarifur Chowdhury
*Assistant Examiner* — Isiaka Akanbi
(74) *Attorney, Agent, or Firm* — Ann Marie Mewherter

(57) ABSTRACT

Computer-implemented methods for inspecting and/or classifying a wafer are provided. One computer-implemented includes detecting defects on a wafer using one or more defect detection parameters, which are determined based on a non-spatially localized characteristic of the wafer that is determined using output responsive to light scattered from the wafer generated by an inspection system. Another computer-implemented method includes classifying a wafer based on a combination of a non-spatially localized characteristic of the wafer determined using output responsive to light scattered from the wafer generated by an inspection system and a spatially localized characteristic of the wafer determined using the output.

38 Claims, 1 Drawing Sheet

U.S. PATENT DOCUMENTS

| | | | |
|---|---|---|---|
| 6,271,916 | B1 | 8/2001 | Marxer et al. |
| 6,538,730 | B2 | 3/2003 | Vaez-Iravani et al. |
| 6,552,337 | B1 | 4/2003 | Cho et al. |
| 6,558,853 | B1 | 5/2003 | Kawamura |
| 6,563,577 | B2 | 5/2003 | Oomori et al. |
| 6,596,553 | B1 | 7/2003 | Lin et al. |
| 6,603,877 | B1 | 8/2003 | Bishop et al. |
| 6,636,031 | B1 | 10/2003 | Kenmochi et al. |
| 6,718,526 | B1 | 4/2004 | Eldredge et al. |
| 6,781,688 | B2 | 8/2004 | Kren et al. |
| 6,794,885 | B1 | 9/2004 | Yasumoto |
| 6,858,859 | B2 | 2/2005 | Kusunose |
| 6,893,786 | B2 | 5/2005 | Baggenstoss |
| 6,898,305 | B2 | 5/2005 | Hiroi et al. |
| 6,917,419 | B2 | 7/2005 | Fielden et al. |
| 6,917,433 | B2 * | 7/2005 | Levy et al. ............... 356/630 |
| 6,919,957 | B2 | 7/2005 | Nikoonahad et al. |
| 7,006,886 | B1 | 2/2006 | Huet et al. |
| 7,038,773 | B2 | 5/2006 | Kuhlmann et al. |
| 7,067,819 | B2 | 6/2006 | Janik |
| 7,286,218 | B2 | 10/2007 | Tiemeyer et al. |
| 7,315,642 | B2 | 1/2008 | Bartov et al. |
| 7,349,079 | B2 | 3/2008 | Zhao et al. |
| 7,359,052 | B2 | 4/2008 | Fielden et al. |
| 7,369,233 | B2 | 5/2008 | Nikoonahad et al. |
| 7,373,277 | B1 | 5/2008 | Wu et al. |
| 7,417,722 | B2 | 8/2008 | Bills et al. |
| 7,528,944 | B2 * | 5/2009 | Chen et al. ............. 356/237.6 |
| 7,751,046 | B2 | 7/2010 | Levy et al. |
| 7,912,658 | B2 * | 3/2011 | Biellak et al. ............... 702/40 |
| 2002/0182760 | A1 | 12/2002 | Wack et al. |
| 2003/0011786 | A1 | 1/2003 | Levy et al. |
| 2003/0107736 | A1 | 6/2003 | Fujimoto |
| 2003/0210393 | A1 | 11/2003 | Vaez-Iravani et al. |
| 2003/0228050 | A1 | 12/2003 | Geshel et al. |
| 2004/0066962 | A1 | 4/2004 | Sasa et al. |
| 2004/0095575 | A1 | 5/2004 | Woo et al. |
| 2004/0252879 | A1 | 12/2004 | Tiemeyer et al. |
| 2005/0094864 | A1 | 5/2005 | Xu et al. |
| 2005/0179910 | A1 | 8/2005 | Bartov |
| 2005/0186670 | A1 | 8/2005 | Oh |
| 2005/0252752 | A1 | 11/2005 | Fielden et al. |
| 2006/0062445 | A1 | 3/2006 | Verma et al. |
| 2006/0091332 | A1 | 5/2006 | Nishiyama et al. |
| 2006/0181700 | A1 | 8/2006 | Andrews et al. |
| 2006/0192948 | A1 | 8/2006 | Judell et al. |
| 2006/0192949 | A1 | 8/2006 | Bills et al. |
| 2006/0192950 | A1 | 8/2006 | Judell et al. |
| 2006/0256326 | A1 | 11/2006 | Bills et al. |
| 2006/0290923 | A1 | 12/2006 | Nakano et al. |
| 2007/0024998 | A1 | 2/2007 | Bills et al. |
| 2007/0156379 | A1 | 7/2007 | Kulkarni et al. |
| 2007/0252977 | A1 | 11/2007 | Baran et al. |
| 2007/0288219 | A1 | 12/2007 | Zafar et al. |
| 2008/0004823 | A1 | 1/2008 | Matsushita et al. |
| 2008/0013083 | A1 | 1/2008 | Kirk et al. |
| 2008/0018887 | A1 | 1/2008 | Chen et al. |
| 2008/0129988 | A1 | 6/2008 | Saito et al. |
| 2008/0205745 | A1 | 8/2008 | Chen et al. |
| 2008/0219545 | A1 | 9/2008 | Chen et al. |
| 2009/0037134 | A1 | 2/2009 | Kulkarni et al. |
| 2009/0299655 | A1 * | 12/2009 | Biellak et al. ............... 702/40 |

FOREIGN PATENT DOCUMENTS

| | | |
|---|---|---|
| JP | 2002-257518 | 9/2002 |
| JP | 2008-096430 | 4/2008 |
| KR | 10-1999-0073971 | 10/1999 |
| KR | 10-2001-0001224 | 1/2001 |
| KR | 10-0738809 | 7/2007 |
| WO | WO 2006/066135 | 6/2006 |
| WO | WO 2006/066136 | 6/2006 |
| WO | WO 2006/066137 | 6/2006 |
| WO | WO 2006/066138 | 6/2006 |
| WO | WO 2006/066139 | 6/2006 |
| WO | WO 2006/066205 | 6/2006 |
| WO | WO 2006/066206 | 6/2006 |
| WO | WO 2006/066207 | 6/2006 |
| WO | WO 2006/066255 | 6/2006 |

OTHER PUBLICATIONS

U.S. Appl. No. 61/074,065 (Chen et al.) entitled Computer-Implemented Methods, Computer-Readable Media, and Systems for Determining One of More Characteristics of a Wafer, filed Jun. 19, 2008.

U.S. Appl. No. 12/128,426 (Biellak et al.) entitled Systems and Methods for Determining Two or More Characteristics of a Wafer, filed Jul. 24, 2008.

Chen et al. "Laser Scattering Correlation with Polysilicon Surface Roughness and Impact on Electical Performance," ISSM 2006.

Elson et al. "Relationship of the total integrated scattering from multilayer-coated optics to angle of incidence, polarization, correlation length, and roughness cross-correlation properties," J.M. et al. Applied Optics, 22, 3207 (1983).

Griffith, J.E. et al.; "Characterization of Scanning Probe Tips for Linewidth Measurement," J. Vac. Sci. Technol. B 9(6), Nov./Dec. 1991, pp. 3586-3589.

Holsteynes et al. "The use of unpatterned wafer inspection for immersion lithography defectivity studies." Apr. 2006.

International Search Report and Written Opinion for PCT/US08/71587 mailed on Dec. 17, 2008.

International Search Report and Written Opinion for PCT/US08/75867 mailed on Feb. 17, 2008.

International Application No. PCT/US05/45781 filed on Dec. 12, 2005.

International Search Report and Written Opinion for PCT/US07/69465 mailed on Sep. 17, 2008.

International Search Report for PCT/US07/61912 mailed Feb. 25, 2008.

Larson, C. Thomas; "Measuring Haze on Deposited Metals with Light-Scattering-Based Inspection Systems," Micro (Sep. 1996), pp. 31-38.

Malik, Igor J. et al. "Surface Roughness of Si Wafers: Correlating AFM and Haze Measurements," Semiconductor Silicon/1994: Seventh International Symposium on Silicon Materials Science and Technology, ed. H.R. Huff, W. Bergholz and K. Sumino, The Electroche.

Marx, Egon et al. "Power spectral densities: A multiple technique study of different Si wafer surfaces," J. Vac. Sci. Technol. B 20(1), Jan./Feb. 2002, pp. 31-41.

McMillan, Wayne; "Surfscan SP2: Enabling Cost-Effective Production and the 65nm Node and Beyond," Yield Management Solutions, Summer 2004, pp. 14-23.

Nemoto et al. "Impact of Silicon Surface Roughness on Device Performance and Novel Roughness Measurement Method," IEEE/SEMI Advanced Semiconductor Manufacturing Conference, 2007.

Scheer, B.W, "Development of a physical haze and microroughness standard," SPIE vol. 2862, pp. 78-95 (1996).

Stover, John C. Optical Scattering: Measurement and Analysis, SPIE Optical Engineering Press, Bellingham, WA (1995).

U.S. Appl. No. 11/855,573 (Wu et al.) entitled Computer-Implemented Methods, Carrier Media, and Systems for Storing Image Data for a Wafer, filed Sep. 14, 2007.

U.S. Appl. No. 11/855,581 (Wu et al.) entitled Computer-Implemented Methods, Carrier Media, and Systems for Displaying an Image of At Least a Portion of a Wafer, filed Sep. 14, 2007.

U.S. Appl. No. 60/868,769 (Fouquet et al.) entitled Methods, Designs, Defect Review Tools, and Systems for Locating Systematic Defects in a Defect Review Process, filed Dec. 6, 2006.

U.S. Appl. No. 60/870,724 (Kulkarni et al.) entitled Methods and Systems for Creating Inspection Recipes Using Design Data, filed Dec. 19, 2006.

U.S. Appl. No. 60/883,617 (Park et al.) entitled Methods and Systems for Using Device Information to Perform One or More Defect-Related Functions, filed Jan. 5, 2007.

Written Opinion and International Search Report for PCT/US2009/045124, mailed Jan. 7, 2010.

Written Opinion and International Search Report for PCT/US2009/051044, mailed Mar. 3, 2010.

* cited by examiner

COMPUTER-IMPLEMENTED METHODS FOR INSPECTING AND/OR CLASSIFYING A WAFER

BACKGROUND OF THE INVENTION

1. Field of the Invention

This invention generally relates to computer-implemented methods for inspecting and/or classifying a wafer. Certain embodiments relate to a method that includes determining one or more defect detection parameters based on a non-spatially localized characteristic of a wafer and/or classifying a wafer based on a combination of a non-spatially localized characteristic of the wafer and a spatially localized characteristic of the wafer.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that generally cannot be determined using inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

There are, however, a number of disadvantages to using metrology processes and tools to measure one or more characteristics of a wafer for process monitoring and control applications. For example, most metrology tools are relatively slow, particularly compared to inspection systems. Therefore, metrology processes are often performed at one location or a limited number of locations on wafers such that metrology results may be acquired in a relatively expedient manner. However, many processes used to manufacture semiconductor devices produce wafers that have characteristic(s) that vary across the surface of the wafers. As such, using metrology measurements performed at one location or a limited number of locations on a wafer may not provide sufficient information about the characteristic(s) of the wafers such that the process can be accurately monitored and controlled. Furthermore, using metrology tools to measure characteristics across the wafer for inline monitoring and control applications is not feasible due to the time in which such measurements can be performed. In particular, metrology measurements performed by currently available metrology tools such as surface roughness, resistivity, film thickness, etc. are not suitable for high sampling of wafers for inline monitoring since the measurements will impact (e.g., increase) cycle time in production.

Attempts have been made to try to use the output generated by inspection systems to determine metrology-like characteristics of wafers. For example, typically, inspection systems are configured with a number of collectors or channels. Each of these collectors or channels is able to capture multiple characteristics of the inspection surface, including, but not limited to, particles and defects of varying shapes and sizes, scratches, surface roughness, film thickness, film composition, film residue, material crystallinity, surface optical constants, nano-feature characteristics, pattern linewidths, and previous process or patterning parameters. While convenient and cost-effective, detecting multiple surface characteristics with a single collector or channel can be sub-optimal. For instance, point defects can scatter substantially strongly into a dark field (DF) collector in some cases, and dynamic range limitations of hardware or software may not permit optimal detection of a different wafer characteristic with that particular collector (e.g., relatively low amplitude, relatively long spatial frequency variations of surface roughness).

In many DF inspection systems, the background surface scattering (haze) or pattern noise is utilized to determine a threshold, either global or local, for defect detection. Defects are often particles, pits, scratches, missing material, or other features tightly confined in at least one spatial dimension. The number, type, size, and/or spatial location of the defects detected by this threshold operation are then recorded, and from this information, a determination of an overall attribute of the wafer (e.g. quality) is made.

In the above described method, many wafer characteristics measurable by the inspection system are largely ignored in dispositioning the wafer. These characteristics can include surface roughness, morphology, film thickness, film composition, film residue, and other previous process-induced changes across the wafer surface. In some cases, these characteristics are utilized for "off-line" analysis after inspection. The utilization and/or data processing of these low spatial frequency characteristics is often independent of the high spatial frequency (e.g., point defect) sample characteristics.

Accordingly, it would be advantageous to develop computer-implemented methods for inspecting and/or classifying a wafer that include determining one or more defect detection parameters based on a non-spatially localized characteristic of a wafer and/or classifying a wafer based on a combination of a non-spatially localized characteristic of the wafer and a spatially localized characteristic of the wafer.

SUMMARY OF THE INVENTION

The following description of various computer-implemented method embodiments is not to be construed in any way as limiting the subject matter of the appended claims.

One embodiment relates to a computer-implemented method for inspecting a wafer. The method includes determining a first characteristic of the wafer using output responsive to light scattered from the wafer generated by an inspection system. The first characteristic is not spatially localized in two dimensions (e.g., in that its lateral scales in two dimensions are larger than a point spread function of the system). The method also includes determining one or more defect detection parameters based on the first characteristic. In addition, the method includes detecting defects on the wafer using the one or more defect detection parameters and the output. The defects are spatially localized in at least one dimension (e.g., in that its lateral scale is smaller than the point spread function of the system in at least one dimension).

In one embodiment, the output used to determine the first characteristic includes output responsive to the light scattered due to haze. In another embodiment, the output used to determine the first characteristic includes output responsive to the light scattered due to pattern noise.

In one embodiment, the first characteristic includes surface roughness, surface roughness variation across the wafer, film thickness, film composition, film residue, one or more pattern dimensions, surface composition, morphology, or morphology changes in the wafer. In another embodiment, the first characteristic includes surface roughness variations over only a subset of all surface spatial frequency bands of surface roughness. In an additional embodiment, the first characteristic is not spatially localized in two dimensions in that lateral scales of the first characteristic in two dimensions are larger than a point spread function of the system.

In one embodiment, determining the one or more defect detection parameters includes determining the one or more defect detection parameters globally for the wafer. In another embodiment, determining the one or more defect detection parameters includes determining the one or more defect detection parameters locally for different regions of the wafer.

In some embodiments, determining the first characteristic includes determining variation in the first characteristic along one direction across the wafer, and determining the one or more defect detection parameters includes determining the one or more defect detection parameters based on the variation in the first characteristic. In another embodiment, determining the first characteristic includes determining variation in the first characteristic in different regions of the wafer. In one such embodiment, determining the one or more defect detection parameters includes selecting the one or more defect detection parameters for the different regions individually based on the variation in the first characteristic in the different regions. In another such embodiment, determining the one or more defect detection parameters includes determining if detecting the defects will be performed in the different regions individually based on the variation in the first characteristic in the different regions.

In one embodiment, the output used to determine the first characteristic includes only a portion of the output generated by the inspection system for the wafer, and the output used to detect the defects on the wafer includes a different portion of the output generated by the inspection system for the wafer. In one such embodiments the portion of the output used to determine the first characteristic and the different portion of the output used to detect the defects are generated by different configurations of illumination and collection subsystems of the inspection system. In another embodiment, the output used to determine the first characteristic and the output used to detect the defects on the wafer is generated by the same configuration of illumination and collection subsystems of the inspection system.

In one embodiment, the method includes classifying the wafer based on a combination of the first characteristic and the defects.

Each of the steps of each of the embodiments of the computer-implemented method described above may be further performed as described herein. In addition, each of the embodiments of the computer-implemented method described above may include any other step(s) of any other method(s) described herein. Furthermore, each of the embodiments of the computer-implemented method described above may be performed by any of the systems described herein.

Another embodiment relates to a computer-implemented method for classifying a wafer. The method includes determining a first characteristic of the wafer using output responsive to light scattered from the wafer generated by an inspection system. The first characteristic is not spatially localized in two dimensions. The method also includes determining a second characteristic of the wafer using the output. The second characteristic is spatially localized in at least one dimension. The method further includes classifying the wafer based on a combination of the first characteristic and the second characteristic.

In one embodiment, the first characteristic is not spatially localized in two dimensions in that lateral scales of the first characteristic in two dimensions are larger than a point spread function of the system. In another embodiment, the first characteristic includes surface roughness, surface roughness variation across the wafer, film thickness, film composition, film residue, one or more pattern dimensions, surface composition, morphology, or morphology changes in the wafer. In an additional embodiment, the second characteristic includes defects on the wafer, and classifying the wafer is performed alter the defects are detected using the output.

In one embodiment, the combination of the first and second characteristics is generated by treating the first and second characteristics equally such that classifying the wafer is equally based on the first and second characteristics.

In one embodiment, classifying the wafer includes determining one or more actions to be performed on the wafer. In another embodiment, classifying the wafer includes determining an overall attribute of the wafer. In an additional embodiment, classifying the wafer includes determining an attribute of a process used to create at least a portion of the wafer.

In one embodiment, classifying the wafer includes classifying the wafer based on the combination of an existence or absence of the first characteristic in one or more spatial locations on the wafer and an existence or absence of the second characteristic in the one or more spatial locations. In another embodiment, classifying the wafer includes classifying the wafer based on the combination of a value of the first characteristic in one or more spatial locations on the wafer and a value of the second characteristic in the one or more spatial locations. In an additional embodiment, classifying the wafer includes determining a single characteristic for a location on the wafer based on the combination of the first characteristic at the location on the wafer and the second characteristic at the same location on the wafer and classifying the wafer based on the single characteristic.

In one embodiment, classifying the wafer includes determining if one of the first and second characteristics is present in a region of the wafer and, if the one of the first to and second characteristics is present in the region, classifying the wafer based on only the first or second characteristic that is present. In another embodiment, classifying the wafer includes determining values of the first and second characteristics in a region of the wafer and, based on the values of the first and second characteristics in the region of the wafer, classifying the wafer based on only the first or second characteristic. In a further embodiment, classifying the wafer includes classifying the wafer differently if the first and second characteristics are both present in a region of the wafer than if the first and second characteristics are present in different regions of the wafer and are not both present in the region of the wafer. In an additional embodiment, the first characteristic used for classifying the wafer is determined on the wafer scale, and the second characteristic used for classifying the wafer includes an attribute of the second characteristic determined on the wafer scale.

In one embodiment, the combination of the first and second characteristics includes overlay of the first and second characteristics. In another embodiment, the combination of the first and second characteristics includes region-based overlay of the first and second characteristics. In an additional embodiment, the combination of the first and second characteristics includes a spatial combination of the first and second characteristics. In a further embodiment, the combination of the first and second characteristics includes a statistical combination of the first and second characteristics. The above-described overlay, region-based overlay, spatial combining, and statistical combining may be performed using some combination of values of the first and second characteristics, absences of the first and second characteristics, and presences of the first and second characteristics.

In one embodiment, the method includes determining additional characteristics of the wafer using the output. In one such embodiment, classifying the wafer includes classifying the wafer based on all of the additional characteristics and the combination of the first and second characteristics. In another such embodiment, classifying the wafer includes classifying the wafer based on fewer than all of the additional characteristics and the combination of the first and second characteristics.

In one embodiment, the second characteristic includes defects on the wafer. In one such embodiment, the method includes determining one or more defect detection parameters based on the first characteristic, and determining the second characteristic includes detecting the defects on the wafer using the one or more defect detection parameters and the output.

In one embodiment, the second characteristic includes defects on the wafer, and the method includes classifying the defects based on the first characteristic in an area of the defects. In another embodiment, the second characteristic includes one or more attributes of defects on the wafer, and the method includes classifying the defects based on the first characteristic in an area of the defects in combination with at least one of the one or more attributes of the defects. In an additional embodiment, the method includes determining one or more attributes of the first characteristic based on the second characteristic in an area of the first characteristic.

Each of the steps of each of the embodiments of the computer-implemented method described above may be further performed as described herein. In addition, each of the embodiments of the computer-implemented method described above may include any other step(s) of any other method(s) described herein. Furthermore, each of the embodiments of the computer-implemented method described above may be performed by any of the systems described herein.

BRIEF DESCRIPTION OF THE DRAWINGS

Other objects and advantages of the invention will become apparent upon reading the following detailed description and upon reference to the accompanying drawings in which.

Figure 1:
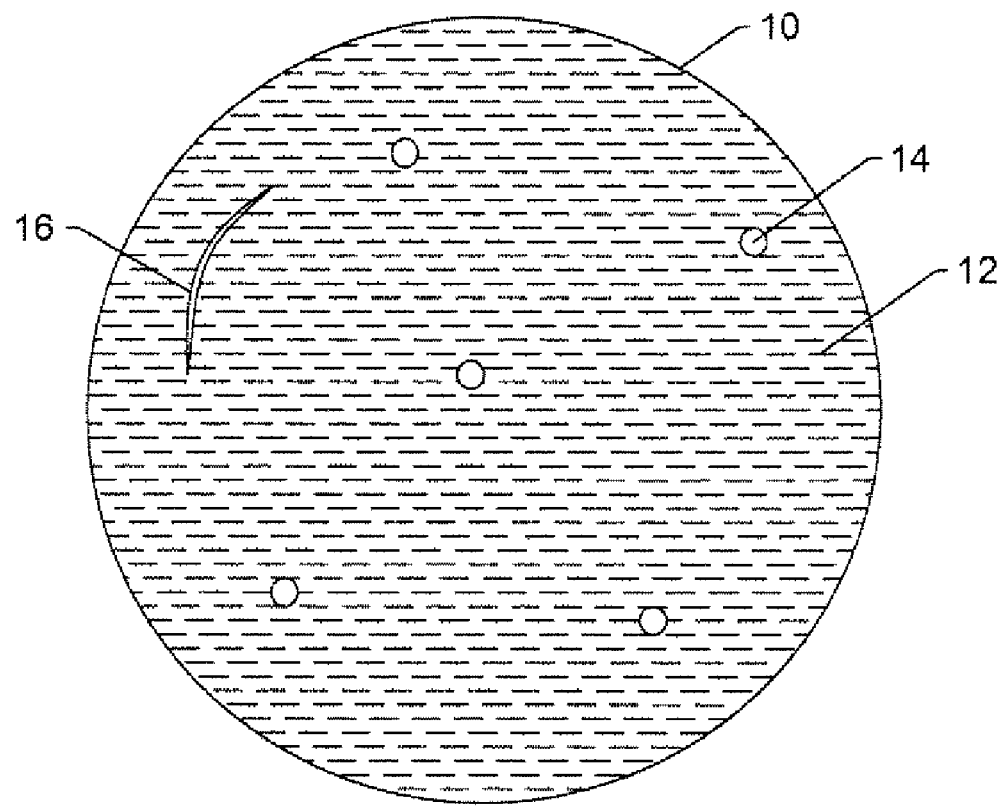
FIG. 1 is a schematic diagram illustrating a plan view of one example of a wafer having two or more characteristics, two characteristics that are spatially localized in at least one dimension and another characteristic that is not spatially localized in two dimensions.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. In this manner, the wafer may be a patterned or an unpatterned wafer. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, the embodiments may be used for inspecting and/or classifying another specimen such as a reticle, which may also be commonly referred to as a mask or a photomask. Many different types of reticles are known in the art, and the terms "reticle," "mask," and "photomask" as used herein are intended to encompass all types of reticles known in the art.

The terms "first" and "second" are used herein to differentiate between different characteristics, etc. The terms "first" and "second" are not used to indicate temporal, spatial, or preferential attributes of the characteristics, etc.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a computer-implemented method for inspecting a wafer. In contrast to the methods described herein, in previously used methods for defect detection, the absence or presence of one or more characteristics such as surface roughness in a particular spatial frequency band would not influence the measurement or detection of another characteristic such as micro-scratches. In contrast, the embodiments described herein allow for improved measurement capability of one characteristic based on another.

The method includes determining a first characteristic of the wafer using output responsive to light scattered from the wafer generated by an inspection system. The output responsive to the light scattered from the wafer may include any suitable output. The inspection system may be configured as described further herein. In one embodiment, the output used to determine the first characteristic includes output responsive to the light scattered due to haze. For example, the first characteristic may be determined based on background surface scattering or haze. In addition, the first characteristic may be determined by haze analysis using commercially available software and/or hardware such as the SU monitor process signature and metrology module and/or the SP2 inspection system, both of which are commercially available from KLA-Tencor, San Jose, Calif. The first characteristic may also be determined using systems and methods described in commonly owned U.S. patent application Ser. No. 11/673,150 by Kirk et al. filed Feb. 9, 2007, which published as U.S. Patent Application Publication No. 2008/0013083 on Jan. 17, 2008, both of which are incorporated by reference as if fully set forth herein. In another embodiment, the output used to determine the first characteristic includes output responsive to the light scattered due to pattern noise. For example, the first characteristic may be determined based on pattern noise. The first characteristic may also be determined using the output and any suitable method and/or algorithm.

The first characteristic is not spatially localized in two dimensions. More specifically, the first characteristic is not spatially localized in two dimensions extending in a plane substantially parallel to the upper surface of the wafer. In other words, the two dimensions are defined in the x-y plane of the wafer. In addition, the first characteristic does not have strong spatial localization in two dimensions. For example, characteristics of wafers that do not have strong spatial localization in two dimensions include surface roughness or the optical constants and thickness of a deposited film and other examples described herein. In this manner, the first characteristic may include a characteristic with scales of tens of microns to mm to cm rather than what is typically known as "defects." In addition, although values of such first characteristics may render the wafer "defective," the characteristics themselves are generally not considered "defects" as that term is commonly used. Instead, such first characteristics are generally considered metrology-like characteristics of the wafer, which can generally not be determined using an inspection system. However, the first characteristic may include a defect or a characteristic of a defect that is not spatially localized in two dimensions. For example, the first characteristic may include a defect that has scales of tens of microns to mm to cm or is otherwise not spatially localized in two dimensions as described herein.

In one embodiment, the first characteristic includes surface roughness, surface roughness variation across the wafer, film thickness, film composition, film residue, one or more pattern dimensions, surface composition, morphology, or morphology changes in the wafer. For example, the first characteristic may include relatively low amplitude, relatively long spatial frequency variations of surface roughness. Therefore, the first characteristic may include a number of different non-spatially localized characteristics of the wafer. In addition, the first characteristic may include any other non-spatially localized characteristic of the wafer that can be determined from the output responsive to the light scattered from the wafer generated by the inspection system. Such first characteristics may be determined using the output and any suitable method and/or algorithm.

In another embodiment, the first characteristic includes surface roughness variations over only a subset of all surface spatial frequency bands of surface roughness. In other words, the first characteristic may include only a portion of all of the surface spatial frequency bands of the surface roughness. As such, the first characteristic may provide more detailed information about the surface roughness than surface roughness of the wafer determined across all surface spatial frequency bands. In particular, when a spot on a wafer having roughness is illuminated, the surface roughness acts like a light grating with the distribution of the surface roughness as a function of the spatial frequency bands. In this manner, when surface roughness is determined across all surface spatial frequency bands, the determined surface roughness represents a single value for the surface roughness that is an average (or another function) of all of the surface spatial frequency bands. In some applications, such characteristics provide less detailed information about the surface roughness. However, by determining the first characteristic for only a portion of all of the surface spatial frequency bands of the surface roughness, more detailed information may be provided about the surface roughness. Such first characteristics can be determined using the output generated by inspection systems such as those described in the patent application by Biellak et al. incorporated by reference below.

In an additional embodiment, the first characteristic is not spatially localized in two dimensions in that lateral scales of the first characteristic in two dimensions are larger than a point spread function of the inspection system. For example, the first characteristic may be a wafer characteristic that can be measured on a length scale much larger than the inspection system point spread function. In one such example, as shown in FIG. 1, wafer 10 may have surface roughness 12. As shown in FIG. 1, the surface roughness is not spatially localized in two dimensions in that the surface roughness extends across substantially the entire surface of wafer 10. Although a first characteristic that is not spatially localized in two dimensions may extend across substantially the entire wafer, the first characteristic may not extend across substantially the entire wafer and may still be not spatially localized in two dimensions (e.g., due to the lateral scale of the first characteristic with respect to the point spread function of the inspection system or the length scale on which the first characteristic can be measured).

In one embodiment, determining the first characteristic includes determining variation in the first characteristic along one direction across the wafer. For example, determining the first characteristic may include determining spatial frequency haze variation along a specific direction of a two-dimensional surface, for instance, due to film thickness. The variation in the first characteristic may be determined across at least a portion of the wafer along the one direction or across an entire dimension of the wafer along the one direction. The variation in the first characteristic along the one direction across the wafer may be determined as one or more values (e.g., average, maximum value, minimum value, standard deviation, etc.) and/or as a function of position along the one direction. Variation in the first characteristic may also be separately determined along more than one direction across the wafer and/or for more than one portion of the wafer. The variation in the first characteristic may be determined as described above using any suitable method and/or algorithm.

In another embodiment, determining the first characteristic includes determining variation in the first characteristic in different regions of the wafer. For example, determining the variation in the first characteristic of the wafer may include determining low spatial frequency haze variation in particular regions of the wafer, for instance, due to film composition or morphology changes. Output responsive to the light scattered from the wafer generated by the inspection system within some portion of the wafer (e.g., only a portion of the wafer, the entire wafer, or the entire portion of the wafer scanned by the inspection system) may be used to determine some variation in the first characteristic in different regions of the wafer. The variation in the first characteristic in the different regions may be determined as one or more values (e.g., average, maximum value, minimum value, standard deviation, etc.) and/or as a function of position across different regions or across the wafer. The different regions in which variation in the first characteristic is determined may extend across the entire wafer, the entire portion of the wafer scanned by the inspection system, or only some portion of the wafer. In addition, some or all of the different regions may be adjacent to one another on the wafer and/or some or all of the different regions may be spaced from one another on the wafer. The different regions may have different shapes and sizes or the same shapes and sizes (e.g., as in a regular grid array of different regions). The shapes and sizes of the different regions may vary depending on, for example, the first characteristic and/or the variation in the first characteristic. For example, the different regions may be determined by analyzing variation in the first characteristic across the wafer such that one different region is defined as an area on the wafer that has values of the first characteristic that are different than values of the first characteristic in other areas on the wafer thereby defined as another different region of the wafer. The variation in the first characteristic may be determined as described above using any suitable method and/or algorithm.

The method may also include storing all of the output responsive to the light scattered from the wafer generated by the inspection system for the entire wafer or the entire portion of the wafer that is scanned during inspection and determining the first characteristic using some or all of the stored output and/or determining the first characteristic as a function of location on the wafer using some or all of the stored output for the wafer. The method may also include determining variation in the first characteristic over the entire wafer, the entire portion of the wafer that is scanned, along one direction of the wafer, or different regions of the wafer as a function of position across the wafer using all or some of the stored output. In addition, the method may include determining one or more attributes of the first characteristic using all or some of the stored output for the wafer (e.g., an average value or some statistical value of the first characteristic across the entire wafer or the entire portion of the wafer). The method may include storing the output using a system such as that described in commonly owned U.S. Patent Application Ser. No. 60/974,030 by Bhaskar et al. filed Sep. 20, 2007, which is incorporated by reference as if fully set forth herein. The embodiments described herein may include any step(s) of any method(s) described in this patent application.

The method also includes determining one or more defect detection parameters based on the first characteristic. As described further herein, the defect detection parameter(s) may be used to detect defects on the wafer that are spatially localized in at least one dimension. In particular, the defects may be spatially localized in one or two dimensions. For example, the defects may include particles and defects of varying shapes and sizes. In addition, the defects may include point defects, particles, pits, scratches, missing material, or other features tightly confined in at least one spatial dimension. Examples of such particles and defects are shown in FIG. 1. In particular, particles 14 and scratch 16 are located on wafer 10. As shown in FIG. 1, particles 14 are localized in two dimensions, and scratch 16 is localized in one dimension. In other words, particles 14 have strong spatial localization in two dimensions, and scratch 16 has strong spatial localization in one dimension. In this manner, the signals produced by such defects will have strong spatial localization in at least one dimension (e.g., a scratch can be centimeters long but is usually much less than one micron wide). The term "defect" as used herein refers specifically to defects that are spatially localized in at least one dimension as opposed to other characteristics of the wafer described herein (the first characteristics) that may render the wafer "defective" but are not themselves considered "defects."

In this manner, in a surface inspection system, wafer characteristic(s) determined in the low spatial frequency regime (e.g., distance scales much larger than the inspection system point spread function) are used to adjust data processing employed to capture or detect higher spatial frequency wafer characteristic(s) such as point defects. In addition, the method may use lower spatial frequency characteristic(s) of the wafer to help optimize the detection of spatially confined defects. The one or more defect detection parameters that are determined based on the first characteristic may include any parameter(s) including any of the parameter(s) described herein of any defect detection method and/or algorithm. In addition, the defect detection parameter(s) may be determined as described further herein using more than one of the first characteristics described herein. Different defect detection parameter(s) may be determined using only one of the first characteristics described herein. Alternatively, different defect detection parameters may be determined using different first characteristics (e.g., one defect detection parameters may be determined based on one of the first characteristics, another defect detection parameter may be determined based on another of the first characteristics, etc.).

In one embodiment, determining the one or more defect detection parameters includes determining the one or more defect detection parameters globally for the wafer. In other words, the one or more defect detection parameters may be determined on a wafer scale and applied globally to the output generated for the wafer for defect detection. In this manner, the determined one or more defect detection parameters may be applied to all of the output generated for the wafer by the inspection system. For example, the one or more defect detection parameters that are determined may include a global threshold to be used for defect detection. In this manner, in a surface inspection system, wafer characteristic(s) determined in the low spatial frequency regime (e.g., distance scales much larger than the inspection system point spread function) may be used to globally adjust data processing employed to capture or detect higher spatial frequency wafer characteristic(s) such as point defects.

In another embodiment, determining the one or more defect detection parameters includes determining the one or more defect detection parameters locally for different regions of the wafer. For example, the one or more defect detection parameters that are determined may include local thresholds to be used for defect detection. In this manner, in a surface inspection system, wafer characteristic(s) determined in the low spatial frequency regime (e.g., distance scales much larger than the inspection system point spread function) may be used to adjust data processing employed to capture or detect higher spatial frequency wafer characteristic(s) such as point defects locally in various wafer regions. The one or more defect detection parameters may be determined independently on any local basis. For example, the one or more defect detection parameters may be determined for one region of the wafer, and the one or more defect detection parameters may be separately determined for another region of the wafer.

As described above, determining the first characteristic may include determining variation in the first characteristic along one direction across the wafer. In one such embodiment, determining the one or more defect detection parameters includes determining the one or more defect detection parameters based on the variation in the first characteristic. For example, variations in low spatial frequency sample characteristic(s) extracted from wafer haze or pattern noise can suggest the optimal inspection system algorithm(s) for detection of spatially confined defects such as scratches, pits, and particles. In one such example, spatial frequency haze variation along a specific direction of a two-dimensional surface, for instance due to film thickness variation, can suggest that a different algorithm be employed for scratch or micro-scratch detection, one which more efficiently filters out the haze variations along that direction. In addition to determining which defect detection algorithm(s) and/or method(s) to use, the variation in the first characteristic can be used to determine any other defect detection parameter(s) (such as values for one or more thresholds of a specific algorithm).

As described above, determining the first characteristic may include determining variation in the first characteristic in different regions of the wafer. In one such embodiment, determining the one or more defect detection parameters includes selecting the one or more defect detection parameters for the different regions individually based on the variation in the first characteristic in the different regions. For example, low spatial frequency haze variation in particular regions of the wafer, for instance due to film composition or morphology changes, can suggest the use of a dynamic point defect detection threshold, in addition to or in place of, a fixed point defect detection threshold in those regions. In addition to determining which defect detection algorithm(s) and/or method(s) to use in different regions of the wafer, the variation in the first characteristic can be used to determine any other defect detection parameter(s) (such as values for one or more thresholds of a specific algorithm) for different regions of the wafer.

In another such embodiment, determining the one or more defect detection parameters includes determining if detecting the defects will be performed in the different regions individually based on the variation in the first characteristic in the different regions. For example, in some cases, a low spatial frequency characteristic in a particular region such as a watermark can suggest that no defect processing should occur in that region in order to avoid false or nuisance defects.

The method also includes detecting defects on the wafer using the one or more defect detection parameters and the output. For example, as described above, the one or more defect detection parameters may include a threshold (e.g., a global or local threshold). In this manner, detecting the defects using the one or more defect detection parameters may include globally or locally applying such a threshold to the output generated by the inspection system. In another example, as described above, the one or more defect detection parameters may include a defect detection method and/or algorithm. Detecting the defects may, therefore, include globally or locally applying the defect detection method and/or algorithm to the output generated by the inspection system for the wafer.

The defect detection parameter(s) are, therefore, determined based on the first characteristic before the defects are detected. For instance, the first characteristic is determined based on the output, the defect detection parameter(s) are determined based on the first characteristic, and then the defects are detected using the output and the defect detection parameter(s). In this manner, the output may be processed twice, once to determine the first characteristic and again to detect the defects.

In some embodiments, the output may be stored as described above such that the output can be reprocessed for defect detection. In such embodiments, as described above, the output generated for the entire wafer, the entire portion of the wafer that is scanned by the inspection system, or some portion of the wafer may be stored. In this manner, the output generated for the entire wafer, the entire portion of the wafer that is scanned by the inspection system, or some portion of the wafer may be processed twice, once to determine the first characteristic and again to detect the defects.

However, output generated for relatively small portions of the wafer may be processed individually to determine the first characteristic for different portions of the wafer and then to detect defects in the different portions. After the output for a relatively small portion of the wafer has been processed to determine the first characteristic and then detect to defects in that portion, that output may be discarded. As such, relatively small amounts of output may be stored in memory at any one point in time thereby reducing the memory requirements of a system used to perform the method.

In one embodiment, the output used to determine the first characteristic includes only a portion of the output generated by the inspection system for the wafer, and the output used to detect the defects on the wafer includes a different portion of the output generated by the inspection system for the wafer. In one such embodiment, the portion of the output used to determine the first characteristic and the different portion of the output used to detect the defects are generated by different configurations of illumination and collection subsystems of the inspection system. The different configurations may be different only in collection (e.g., wide scattering angles vs. narrow scattering angles), illumination (e.g., normal (or near normal) vs. oblique), wavelength, polarization, etc., or some combination thereof. The different portions of the output may be generated by the inspection system concurrently or sequentially. However, the same output may be used to determine the first characteristic and to detect the defects. For example, in one embodiment, the output used to determine the first characteristic and the output used to detect the defects on the wafer is generated by the same configuration of illumination and collection subsystems of the inspection system. In all of the above embodiments, the illumination and collection subsystems of the inspection system may be configured as described in the patent application by Biellak et al. incorporated by reference below.

In some embodiments, the method includes classifying the wafer based on a combination of the first characteristic and the defects. Classifying the wafer based on a combination of the first characteristic and the defects may be performed according to any of the embodiments described further herein.

Each of the embodiments of the computer-implemented method described above may include any other step(s) of any other computer-implemented method(s) described herein. In addition, each of the embodiments of the computer-implemented method described above may be performed by any of the systems described herein.

Another embodiment relates to a computer-implemented method for classifying a wafer. The method includes determining a first characteristic of the wafer using output responsive to light scattered from the wafer generated by an inspection system. The output responsive to the light scattered from the wafer may include any suitable output including the output described further herein. The inspection system may be configured as described herein. The first characteristic may be determined as described herein using the output and any suitable method and/or algorithm. The first characteristic may also be determined on the wafer scale or some local scale as described above.

The first characteristic is not spatially localized in two dimensions. The first characteristic may include any such first characteristics described herein. For example, in one embodiment, the first characteristic is not spatially localized in two dimensions in that lateral scales of the first characteristic in two dimensions are larger than a point spread function of the system. In another embodiment, the first characteristic includes surface roughness, surface roughness variation across the wafer, film thickness, film composition, film residue, one or more pattern dimensions, surface composition, morphology, or morphology changes in the wafer. For example, the first characteristic may include surface roughness, morphology, film thickness, film composition, film residue, and other previous process-induced changes across the wafer surface.

The method also includes determining a second characteristic of the wafer using the output. The second characteristic is spatially localized in at least one dimension. More specifically, the second characteristic is spatially localized in at least one dimension extending in a plane substantially parallel to the upper surface of the wafer. In other words, the at least one dimension is defined in the x-y plane of the wafer. The second characteristic may be spatially localized in at least one dimension in that a lateral scale of the second characteristic in at least one dimension is smaller than a point spread function of the system. For example, the second characteristic may be defects such as point defects that are smaller than the point spread function. In this manner, "spatial localization" means on the order of the system optical point spread function or smaller.

In one embodiment, the second characteristic includes defects on the wafer. The defects are spatially localized in one or two dimensions. For example, the second characteristic may include particles and defects of varying shapes and sizes such as those described above. As such, the method embodiments described herein may be considered "inspection methods" in that at least one characteristic that can be determined using the systems includes "defects" that are commonly detected using inspection methods. The defects may include any of the spatially localized defects described herein such as specific point or extended defects including, but not limited to, particles, pits, scratches, dimples, micro-scratches, etc. For example, the second characteristic may include the presence and size of particles having diameters of 30 nanometers to 1 micrometer on the wafer. However, the second characteristic may include defects on the wafer that have any size that renders the defects detectable by the inspection system (e.g., smaller than 30 nanometers and larger than 1 micrometer). The second characteristic may include any suitable characteristic of the spatially localized defects such as number, types, sizes, and/or spatial locations of the defects.

Determining the second characteristic may include detecting the defects and then determining the second characteristic based on the detected defects. For example, the number, types, sizes, and/or spatial locations of the defects detected (e.g., by applying a threshold to the output) may be determined and recorded. The number, types, sizes, and/or spatial locations of the defects may then be used as the second characteristic. In another example, the second characteristic may be the total number of point defects, irrespective of location on the wafer. Any of the second characteristics described above may be determined using any suitable algorithm(s) and/or method(s).

The method further includes classifying the wafer based on a combination of the first characteristic and the second characteristic. For example, in a surface inspection system, characteristic(s) of a wafer determined over length scales much larger than the system point spread function are combined in the embodiments described herein with characteristic(s) of much smaller spatial extent (such as point defects) in post-inspection data processing to determine a classification of the wafer. In this manner, the method may include utilizing and/or data processing of low spatial frequency characteristic(s) of the wafer in combination with high spatial frequency (e.g., point defect) characteristic(s) of the wafer to classify the wafer. As such, classifying the wafer may be performed using non-spatially localized feature(s) of the wafer in conjunction with other feature(s) of the wafer that are spatially localized in at least one dimension (smaller feature(s) of the wafer). Classifying the wafer according to any of the embodiments described herein may be performed using any suitable method and/or algorithm.

In previously used methods for wafer classification, the various characteristics measured by surface inspection systems were often used independently for wafer dispositioning. For instance, the number of point defects on a wafer in a certain size range would determine whether the wafer was "good" or "bad." That same wafer could have a variation in surface roughness that would also determine the wafer quality, but until now, little or no effort has been made to overlay or otherwise combine these characteristics spatially, statistically, or in any other suitable manner for a more accurate determination of overall wafer quality.

As described above, the second characteristic may include defects on the wafer. In one such embodiment, classifying the wafer is performed after the defects are detected using the output. For example, once algorithm(s) and/or other data processing are utilized to determine the wafer characteristics in all locations of interest on the wafer, the first and second characteristics determined for all or some of the locations of interest can be used to disposition or classify the wafer. In this manner, the embodiments described herein are different than methods for classifying individual defects on a wafer at least in that classifying a wafer does not refer to classifying individual defects on the wafer (although classifications determined for individual defects may be used to determine an overall classification for the wafer).

In one embodiment, the combination of the first and second characteristics is generated by treating the first and second characteristics equally such that classifying the wafer is equally based on the first and second characteristics. For example, the method may include treating the measured lower spatial frequency characteristic(s) of the wafer equally with the measured spatially confined defect characteristic(s) for post-inspection wafer dispositioning. In this manner, the method may treat all characteristics of the wafer that can be measured by the SURFmonitor module on equal footing with "classic" defects typically measured on SURFscan tools, which are commercially available from KLA-Tencor.

In another embodiment, classifying the wafer includes determining an overall attribute of the wafer. For example, in a surface inspection system, characteristic(s) of a wafer determined over length scales much larger than the system point spread function may be combined with characteristic(s) of much smaller spatial extent (such as point defects) in post-inspection data processing to determine an attribute of the wafer. In addition, the combination of the first and second characteristics may be used to determine an overall attribute of the wafer (e.g., the quality of the wafer).

In one embodiment, classifying the wafer includes determining one or more actions to be performed on the wafer. For example, classifying the wafer may include dispositioning the wafer. Dispositioning may include determining an overall sample attribute such as the suitability of the wafer for further expensive processing. In this manner, the one or more actions to be performed on the wafer may be determined for the wafer dispositioning. Such actions may include, but are not limited to, repair, rework, discard, and process further. In this manner, the methods described herein may be surface inspection methods utilizing multiple wafer characteristics to improve wafer dispositioning. In addition, the methods described herein provide improved surface inspection methods that measure multiple disparate characteristics of a wafer and utilize some or all of the measured characteristics to disposition the sample.

In an additional embodiment, classifying the wafer includes determining an attribute of a process used to create at least a portion of the wafer. For example, in a surface inspection system, characteristic(s) of a wafer determined over length scales much larger than the system point spread function may be combined with characteristic(s) of much smaller spatial extent (such as point defects) in post-inspection data processing to determine an attribute of the process used to create the wafer. The attribute of the process used to create the wafer may include, for example, whether or not the process is performing within specifications, whether or not the process is drifting out of specifications, whether or not the process is failing, and whether or not the process should be evaluated.

In one embodiment, classifying the wafer includes classifying the wafer based on the combination of an existence or absence of the first characteristic in one or more spatial locations on the wafer and an existence or absence of the second characteristic in the one or more spatial locations. For example, the existence or absence of one or more characteristics such as spatially confined defects and lower spatial frequency information such as surface roughness variation, film thickness, film composition, film residue, pattern line widths, surface composition and morphology changes in one or more spatial locations can be used to disposition or classify the wafer. The existence or absence of the first characteristic in the one or more spatial locations can be determined by applying a threshold to the first characteristic in the one or more spatial locations, and the existence or absence of the second characteristic in the one or more spatial locations can be determined by applying a threshold to the second characteristic in the one or more spatial locations. In this manner, the first and second characteristics may be used after thresholding of the first and/or second characteristic to classify the wafer. The one or more spatial locations may include any spatial location(s) on the wafer.

In another embodiment, classifying the wafer includes classifying the wafer based on the combination of a value of the first characteristic in one or more spatial locations on the wafer and a value of the second characteristic in the one or more spatial locations. For example, the values of one or more characteristics such as spatially confined defects and lower spatial frequency information such as surface roughness variation, film thickness, film composition, film residue, pattern line widths, surface composition and morphology changes in one or more spatial locations can be used to disposition or classify the wafer. The values of the first and second characteristics in the one or more spatial locations can be determined based on spatial information about the first and second characteristics on the wafer without applying a threshold to the first and second characteristics. In this manner, the first and second characteristics may be used before thresholding of the first and second characteristics to classify the wafer. The one or more spatial locations may include any spatial location(s) on the wafer.

In some embodiments, classifying the wafer includes determining a single characteristic for a location on the wafer based on the combination of the first characteristic at the location on the wafer and the second characteristic at the same location on the wafer and classifying the wafer based on the single characteristic. For example, a multitude of different characteristics, for instance point defects and increased surface roughness, in a single location can be combined or binned into a single characteristic that is the superset of the individual characteristics. The single characteristic can then be used to classify the wafer.

In another embodiment classifying the wafer includes determining if one of the first and second characteristics is present in a region of the wafer and, if the one of the first and second characteristics is present in the region, classifying the wafer based on only the first or second characteristic that is present. For example, for classification purposes, one of the characteristics may be ignored in a region where one or more other characteristics are present. The region of the wafer may include any suitable region of the wafer (e.g., only a portion of the area of the wafer). Determining if one of the first and second characteristics is present in a region of the wafer may be performed separately for different regions of the wafer. In addition, classifying the wafer may be performed based on only the first or second characteristic that is present in different regions of the wafer.

In some embodiments, classifying the wafer includes determining values of the first and second characteristics in a region of the wafer and, based on the values of the first and second characteristics in the region of the wafer, classifying the wafer based on only the first or second characteristic. For example, for classification purposes, one of the characteristics may be ignored in a region where one or more other characteristics have certain values. The region of the wafer may include any suitable region of the wafer (e.g., only a portion of the area of the wafer). Determining values of the first and second characteristics in a region of the wafer may be performed separately for different regions of the wafer. In addition, depending on the values of the first and second characteristics in corresponding regions of the wafer, classifying the wafer may be performed based on only the first or second characteristic in different regions of the wafer.

In an additional embodiment, classifying the wafer includes classifying the wafer differently if the first and second characteristics are both present in a region of the wafer than if the first and second characteristics are present in different regions of the wafer and are not both present in the region of the wafer. For example, two or more characteristics in the same region of a wafer can cause the wafer to be classified differently than the same two or more characteristics present in different regions of the sample.

In one embodiment, the first characteristic used for classifying the wafer is determined on the wafer scale, and the second characteristic used for classifying the wafer includes an attribute of the second characteristic determined on the wafer scale. For example, a second characteristic such as the total number of point defects, irrespective of location, detected on the wafer can be combined with a first characteristic such as, for example, the total surface area where an unwanted film or feature, such as a watermark, is present to classify the wafer. In one such example, the number of point defects on a particular wafer could be relatively low, and on that basis alone the wafer may "pass" inspection. However, the same wafer may have substantially large non-spatially localized type features. The combination of the two characteristics (the first characteristic indicating the substantially large non-spatially localized type features and the second characteristic indicating the relatively low number of point defects on the wafer) could trigger a "fail" result.

In some embodiments, the combination of the first and second characteristics includes overlay of the first and second characteristics. For example, in a surface inspection system, characteristic(s) of a wafer determined over length scales much larger than the system point spread function may be combined with characteristic(s) of much smaller spatial extent (such as point defects) in post-inspection data processing using overlay to determine a classification of the wafer. In one such example, a set of point defect results may be overlaid with a set of non-spatially localized feature results. The characteristics that are overlaid may include any of the first and second characteristics described herein, one or more attributes of the first characteristic and one or more attributes of the second characteristic, the first characteristic and one or more attributes of the second characteristic, or one or more attributes of the first characteristic and the second characteristic. For example, results "statistics" for the first and/or second characteristic for the entire wafer may be overlaid with each other or with the other characteristic. In addition, overlay may be performed using some combination of values of the first and second characteristics, absences of the first and second characteristics, and presences of the first and second characteristics. For example, overlay may be performed using some combination of results of applying a threshold to the first characteristic, results of applying a threshold to the second characteristic, the first characteristic without application of a threshold thereto (e.g., before thresholding of the first characteristic), and the second characteristic without application of a threshold thereto (e.g., before thresholding of the second characteristic. Overlay may be performed for the entire wafer or the entire portion of the wafer that is scanned during inspection. Alternatively, overlay may be performed for only a portion of the wafer or only a portion of the wafer that is scanned during inspection. In this manner, the combination may include overlay of the first and second characteristics on a wafer scale or on a local scale. Overlay of the first and second characteristics may be performed using any suitable algorithm(s) and/or method(s).

In another embodiment, the combination of the first and second characteristics includes region-based overlay of the first and second characteristics. For example, in a surface inspection system, characteristic(s) of a wafer determined over length scales much larger than the system point spread function may be combined with characteristic(s) of much smaller spatial extent (such as point defects) in post-inspection data processing using region-based overlay to determine a classification of the wafer. In one such example, a set of point defect results may be overlaid with a set of non-spatially localized feature results in relatively small regions or areas of the wafer. The characteristics that are overlaid on a region basis may include any of the first and second characteristics described herein, one or more attributes of the first characteristic and one or more attributes of the second characteristic, the first characteristic and one or more attributes of the second characteristic, or one or more attributes of the first characteristic and the second characteristic. For example, results "statistics" for the first and/or second characteristic determined for a region of the wafer may be overlaid with each other or with the other characteristic. In addition, region-based overlay may be performed using some combination of values of the first and second characteristics, absences of the first and second characteristics, and presences of the first and second characteristics. For example, region-based overlay may be performed using some combination of results of applying a threshold to the first characteristic, results of applying a threshold to the second characteristic, the first characteristic without application of a threshold thereto (e.g., before thresholding of the first characteristic), and the second characteristic without application of a threshold thereto (e.g., before thresholding of the second characteristic). Region-based overlay of the first and second characteristics may be performed using any suitable algorithm(s) and/or method(s).

Region-based overlay may be performed for only one region of the wafer or more than one region of the wafer (e.g., only the regions of interest on the wafer). The region(s) of the wafer for which overlay is performed may in combination extend across the entire wafer or the entire portion of the wafer that is scanned during inspection or may extend across only a portion of the entire wafer or only a portion of the wafer that is scanned during inspection. In addition, the region(s) of the wafer for which overlay is performed may be determined based on one or more of the characteristics. For example, the method may include analyzing the second characteristic such as a number of point defects detected in different regions of the wafer to identify regions of the wafer in which the number of point defects is relatively high and then performing overlay in only those regions in which the number of point defects is relatively high (e.g., to determine if the number of point defects corresponds to some non-spatially localized characteristic of the wafer).

In an additional embodiment, the combination of the first and second characteristics includes a spatial combination of the first and second characteristics. For example, a spatial combination of the first and second characteristics may include overlay of the first and second characteristics as described above (overlay on a spatial basis). However, a spatial combination of the first and second characteristics does not necessarily include overlay. For example, the first and second characteristics can be combined mathematically or otherwise for individual locations on the wafer (e.g., on a spatial basis). The first and second characteristics for individual locations on the wafer may be combined in any other suitable manner. In addition, the spatial combination of the first and second characteristics may be generated based on some combination of values of the first and second characteristics, absences of the first and second characteristics, and presences of the first and second characteristics. For example, the spatial combination may be generated based on some combination of results of applying a threshold to the first characteristic, results of applying a threshold to the second characteristic, the first characteristic without application of a threshold thereto (e.g., before thresholding of the first characteristic), and the second characteristic without application of a threshold thereto (e.g., before thresholding of the second characteristic).

In a further embodiment, the combination of the first and second characteristics includes a statistical combination of the first and second characteristics. The first and second characteristics may be combined statistically in any suitable manner. In addition, the statistical combination of the first and second characteristics may be generated based on some combination of values of the first and second characteristics, absences of the first and second characteristics, and presences of the first and second characteristics. For example, the statistical combination may be generated based on some combination of results of applying a threshold to the first characteristic, results of applying a threshold to the second characteristic, the first characteristic without application of a threshold thereto (e.g., before thresholding of the first characteristic), and the second characteristic without application of a threshold thereto (e.g., before thresholding of the second characteristic).

In one embodiment, the method includes determining additional characteristics of the wafer using the output. The additional characteristics may include one or more additional characteristics that are not spatially localized and/or one or more additional characteristics that are spatially localized in at least one dimension. For example, the first characteristic may include surface roughness variations across the wafer, the second characteristic may include a characteristic of particles on the wafer, and the additional characteristic may include variations in the thickness of a film on the wafer. In another example, the first characteristic may include variations in the thickness of a film on the wafer, the second characteristic may include a characteristic of particles on the wafer, and the additional characteristic may include a characteristic of pits on the wafer.

In one such embodiment, classifying the wafer includes classifying the wafer based on all of the additional characteristics and the combination of the first and second characteristics. For example, in a surface inspection system, characteristic(s) of a wafer determined over length scales much larger than the system point spread function may be combined with characteristic(s) of much smaller spatial extent (such as point defects) in post-inspection data processing of all of the characteristics measured. In another such embodiment, classifying the wafer includes classifying the wafer based on fewer than all of the additional characteristics and the combination of the first and second characteristics. For example, in a surface inspection system, characteristic(s) of a wafer determined over length scales much larger than the system point spread function may be combined with characteristic(s) of much smaller spatial extent (such as point defects) in post-inspection data processing of only some of the characteristics measured.

As described above, in one embodiment, the second characteristic includes defects on the wafer. In one such embodiment, the method includes determining one or more defect detection parameters based on the first characteristic. Determining the one or more defect detection parameters based on the first characteristic may be performed as described further herein. In one such embodiment, determining the second characteristic includes detecting the defects on the wafer using the one or more defect detection parameters and the output. Detecting the defects on the wafer using the one or more defect detection parameters and the output may be performed as described further herein. The second characteristic may be determined based on the detected defects as described further herein.

In one embodiment, the second characteristic includes defects on the wafer. The second characteristic may include defects on the wafer as described above. In one such embodiment, the method includes classifying the defects based on the first characteristic in an area of the defects. In this manner, the method may include classifying one characteristic based on the other. Classifying the defects may include determining the defect type of the defects. For example, the type of point defects (included in the second characteristic) may be determined based on the first characteristic in the area of the defects (e.g., local values of the first characteristic). The first characteristic in the area of the defects may include value(s) of the first characteristic that are spatially coincident with the defects (e.g., in the same area in which the defects are located). However, the first characteristic in the area of the defects may include value(s) of the first characteristic that are near the defects (e.g., within about 1 micron of the defects). Classifying the defects based on the first characteristic as described above may be performed using any suitable algorithm and/or method.

In another embodiment, the second characteristic includes one or more attributes of defects on the wafer, and the method includes classifying the defects based on the first characteristic in an area of the defects in combination with at least one of the one or more attributes of the defects. For example, the one or more attributes of the defects on the wafer may include size of the defects in one or more dimensions and/or any other attribute(s) of defects described herein. The attribute(s) of the defects may be determined using the output generated by the inspection system and any suitable algorithm and/or method. In this manner, this embodiment of the method may also include classifying one characteristic based on the other. Classifying the defects may include determining the defect type of the defects. For example, the type of point defects (included in the second characteristic) may be determined based on the first characteristic in the area of the defects (e.g., local values of the first characteristic) in combination with one or more attributes (e.g., size) of the defects. The first characteristic in the area of the defects may include any of such first characteristics described above. Classifying the defects based on the first characteristic in the area of the defects in combination with at least one attribute of the defects may be performed using any suitable algorithm and/or method.

In an additional embodiment, the method includes determining one or more attributes of the first characteristic based on the second characteristic in an area of the first characteristic. For example, the method may include classifying the first characteristic based on the second characteristic in the area of the first characteristic. In this manner, the method may include classifying one characteristic based on the other. Classifying the first characteristic may include determining the defect type or other type of the first characteristic. In another example, the method may include determining a cause of the first characteristic based on the second characteristic in the area of the first characteristic. In such examples, the spatially constrained second characteristic may help clarify the cause of the first spatially extended characteristic. In one particular example, the presence of particles on a resist on a wafer may be related to thickness variations of the resist on the wafer (e.g., if the particles prevent substantially uniform coating of the resist on the wafer). Therefore, the presence of the particles on the wafer and their spatial relationship to the thickness variations may help clarify the cause of the thickness variations (e.g., the presence of the particles themselves). The second characteristic in the area of the first characteristic may include value(s) of the second characteristic that are spatially coincident with the first characteristic (e.g., in the same area as the first characteristic or in the same area as local values of the first characteristic). However, the second characteristic in the area of the first characteristic may include value(s) of the second characteristic that are near the first characteristic or near local values of the first characteristic (e.g., within about 1 micron of the first characteristic or within about 1 micron of the local values of the first characteristic). Determining the one or more attributes of the first characteristic may also be performed based on the second characteristic in the area of the first characteristic in combination with one or more other attributes of the first characteristic (e.g., spatial extent, shape, variation as a function of wafer position, etc.). Classifying the first characteristic based on the second characteristic as described above may be performed using any suitable algorithm and/or method.

Each of the embodiments of the computer-implemented method described above may include any other step(s) of any other computer-implemented method embodiment(s) described herein. In addition, each of the embodiments of the computer-implemented method described above may be performed by any of the systems described herein.

Figure 2:
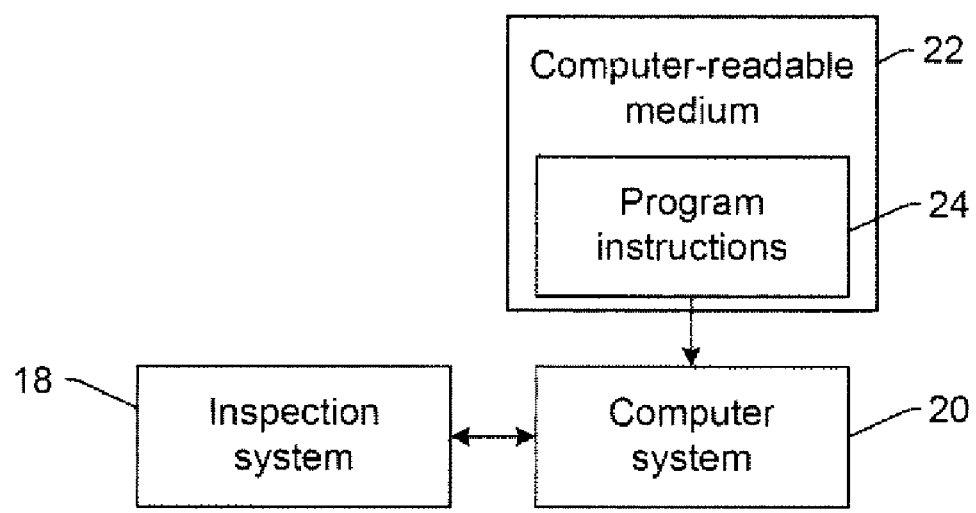
FIG. 2 is a block diagram illustrating one embodiment of a system configured to perform one or more computer-implemented methods described herein and one embodiment of a computer-readable medium that includes program instructions executable on a computer system for performing one or more computer-implemented methods described herein.

FIG. 2 illustrates one embodiment of a system that can perform one or more computer-implemented methods described herein. The system includes inspection system 18. The inspection system is configured to generate output responsive to light scattered from a wafer. The inspection system may be configured as described in commonly owned U.S. patent application Ser. No. 12/128,426 by Biellak et al. filed May 28, 2008, which is incorporated by reference as if fully set forth herein. In addition, the inspection system may be configured as described in U.S. Pat. No. 7,286,218 to Judell et al., which is incorporated by reference as if fully set forth herein. Furthermore, the methods described herein may be implemented using an existing inspection system (e.g., by modifying an existing inspection system based on the embodiments described herein) such as the SPx series of tools. For some such systems, the functionality of the method embodiments described herein may be provided as optional functionality of the system (e.g., in addition to other functionality of the system).

The system also includes computer system 20. The output generated by the inspection system may be provided to the computer system. For instance, the computer system may be coupled to the inspection system (e.g., to one or more detectors or detection subsystems of the inspection system) such that the computer system can receive the output generated by the inspection system. The computer system may be configured to perform any step(s) of any of the computer-implemented method embodiment(s) described herein using the output. For instance, the computer system may be configured to determine a first characteristic of the wafer using the output. The first characteristic may include any of the first characteristics described herein. The computer system may also be configured to determine one or more defect detection parameters based on the first characteristic. The one or more defect detection parameters may include any of the defect detection parameter(s) described herein. In addition, the computer system may be configured to detect defects on the wafer using the one or more defect detection parameters and the output. The defects may include any of the defects described herein. The computer system may be configured to perform such steps (and any other step(s) of any other computer-implemented method embodiment(s) described herein) as described further herein.

The computer system may take various forms, including a personal computer system, image computer, mainframe computer system, workstation network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

The computer system may be a computer system included in the inspection system or may be a computer system external to the inspection system (but coupled to the inspection system or a computer system of the inspection system as described above such that the computer system can receive the output generated by the inspection system). For example, the computer system described above may be configured as a stand-alone system that does not form part of an inspection, metrology, review, or other tool. In such an embodiment, the computer system may be configured to receive and/or acquire data or information from other systems (e.g., output generated by the inspection system) by a transmission medium that may include "wired" and/or "wireless" portions. In this manner, the transmission medium may serve as a data link between the computer system and the other system. In addition, the computer system may send data to the other system via the transmission medium. Such data may include any of the results of the methods described herein.

Another embodiment relates to a computer-readable medium that includes program instructions executable on a computer system for performing one or more computer-implemented method embodiments described herein. One such embodiment is shown in FIG. 2. For example, as shown in FIG. 2, computer-readable medium 22 includes program instructions 24 executable on computer system 20 for performing one or more of the computer-implemented method embodiments described herein.

Program instructions 24 implementing methods such as those described herein may be transmitted over or stored on computer-readable medium 22. The computer-readable medium may be a transmission medium such as a wire, cable, or wireless transmission link. The computer-readable medium may also be a storage medium such as a read-only memory, a RAM, a magnetic or optical disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C+objects, C#, JavaBeans, Microsoft Foundation Classes ("MFC"), or other technologies or methodologies, as desired.

The embodiments described herein may also include storing results of one or more steps of one or more computer-implemented methods described herein in a storage medium. The results may include any of the results described herein. The results may be stored in any manner known in the art. The storage medium may include any suitable storage medium known in the art. After the results have been stored, the results can be accessed in the storage medium and used by any of the method or system embodiments described herein, any other method, or any other system. Furthermore, the results may be stored "permanently," "semi-permanently," temporarily, or for some period of time. For example, the storage medium may be random access memory (RAM), and the results may not necessarily persist indefinitely in the storage medium.

Further modifications and alternative embodiments of various aspects of the invention may be apparent to those skilled in the art in view of this description. For example, computer-implemented methods for inspecting and/or classifying a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for inspecting a wafer, comprising:
   determining a first characteristic of the wafer using output responsive to light scattered from the wafer generated by an inspection system, wherein the first characteristic is not spatially localized in two dimensions;
   determining one or more defect detection parameters based on the first characteristic; and
   detecting defects on the wafer by applying the one or more defect detection parameters to the output, wherein the defects are spatially localized in at least one dimension.

2. The method of claim 1, wherein the output used to determine the first characteristic comprises output responsive to the light scattered due to haze.

3. The method of claim 1, wherein the output used to determine the first characteristic comprises output responsive to the light scattered due to pattern noise.

4. The method of claim 1, wherein the first characteristic comprises surface roughness, surface roughness variation across the wafer, film thickness, film composition, film residue, one or more pattern dimensions, surface composition, morphology, or morphology changes in the wafer.

5. The method of claim 1, wherein the first characteristic comprises surface roughness variations over only a subset of all surface spatial frequency bands of surface roughness.

6. The method of claim 1, wherein the first characteristic is not spatially localized in two dimensions in that lateral scales of the first characteristic in two dimensions are larger than a point spread function of the system.

7. The method of claim 1, wherein determining the one or more defect detection parameters comprises determining the one or more defect detection parameters globally for the wafer.

8. The method of claim 1, wherein determining the one or more defect detection parameters comprises determining the one or more defect detection parameters locally for different regions of the wafer.

9. The method of claim 1, wherein determining the first characteristic comprises determining variation in the first characteristic along one direction across the wafer, and wherein determining the one or more defect detection parameters comprises determining the one or more defect detection parameters based on the variation in the first characteristic.

10. The method of claim 1, wherein determining the first characteristic comprises determining variation in the first characteristic in different regions of the wafer, and wherein determining the one or more defect detection parameters comprises selecting the one or more defect detection parameters for the different regions individually based on the variation in the first characteristic in the different regions.

11. The method of claim 1, wherein determining the first characteristic comprises determining variation in the first characteristic in different regions of the wafer, and wherein determining the one or more defect detection parameters comprises determining if detecting the defects will be performed in the different regions individually based on the variation in the first characteristic in the different regions.

12. The method of claim 1, wherein the output used to determine the first characteristic comprises only a portion of the output generated by the inspection system for the wafer, wherein the output used to detect the defects on the wafer comprises a different portion of the output generated by the inspection system for the wafer, and wherein the portion of the output used to determine the first characteristic and the different portion of the output used to detect the defects are generated by different configurations of illumination and collection subsystems of the inspection system.

13. The method of claim 1, wherein the output used to determine the first characteristic and the output used to detect the defects on the wafer is generated by the same configuration of illumination and collection subsystems of the inspection system.

14. The method of claim 1, further comprising classifying the wafer based on a combination of the first characteristic and the detects.

15. A computer-implemented method for classifying a wafer, comprising:
   determining a first characteristic of the wafer using output responsive to light scattered from the wafer generated by an inspection system, wherein the first characteristic is not spatially localized in two dimensions;
   determining one or more defect detection parameters based on the first characteristic;
   determining a second characteristic of the wafer using the output, wherein the second characteristic is spatially localized in at least one dimension, wherein the second characteristic comprises defects on the wafer, and wherein determining the second characteristic comprises detecting the defects on the wafer by applying the one or more defect detection parameters to the output; and
   classifying the wafer based on a combination of the first characteristic and the second characteristic.

16. The method of claim 15, wherein the first characteristic is not spatially localized in two dimensions in that lateral scales of the first characteristic in two dimensions are larger than a point spread function of the system.

17. The method of claim 15, wherein the first characteristic comprises surface roughness, surface roughness variation across the wafer, film thickness, film composition, film residue, one or more pattern dimensions, surface composition, morphology, or morphology changes in the wafer.

18. The method of claim 15, wherein said classifying is performed after the detects are detected using the output.

19. The method of claim 15, wherein the combination of the first and second characteristics is generated by treating the first and second characteristics equally such that said classifying is equally based on the first and second characteristics.

20. The method of claim 15, wherein said classifying comprises determining one or more actions to be performed on the wafer.

21. The method of claim 15, wherein said classifying comprises determining an overall attribute of the wafer.

22. The method of claim 15, wherein said classifying comprises determining an attribute of a process used to create at least a portion of the wafer.

23. The method of claim 15, wherein said classifying comprises classifying the wafer based on the combination of an existence or absence of the first characteristic in one or more spatial locations on the wafer and an existence or absence of the second characteristic in the one or more spatial locations.

24. The method of claim 15, wherein said classifying comprises classifying the wafer based on the combination of a value of the first characteristic in one or more spatial locations on the wafer and a value of the second characteristic in the one or more spatial locations.

25. The method of claim 15, wherein said classifying comprises determining a single characteristic for a location on the wafer based on the combination of the first characteristic at the location on the wafer and the second characteristic at the same location on the wafer and classifying the wafer based on the single characteristic.

26. The method of claim 15, wherein said classifying comprises determining if one of the first and second characteristics is present in a region of the wafer and, if the one of the first and second characteristics is present in the region, classifying the wafer based on only the first or second characteristic that is present.

27. The method of claim 15, wherein classifying the wafer comprises determining values of the first and second characteristics in a region of the wafer and, based on the values of the first and second characteristics in the region of the wafer, classifying the wafer based on only the first or second characteristic.

28. The method of claim 15, wherein said classifying comprises classifying the wafer differently if the first and second characteristics are both present in a region of the wafer than if the first and second characteristics are present in different regions of the wafer and are not both present in the region of the wafer.

29. The method of claim 15, wherein the first characteristic used for said classifying is determined on the wafer scale, and wherein the second characteristic used for said classifying comprises an attribute of the second characteristic determined on the wafer scale.

30. The method of claim 15, wherein the combination of the first and second characteristics comprises overlay of the first and second characteristics.

31. The method of claim 15, wherein the combination of the first and second characteristics comprises region-based overlay of the first and second characteristics.

32. The method of claim 15, wherein the combination of the first and second characteristics comprises a spatial combination of the first and second characteristics.

33. The method of claim 15, wherein the combination of the first and second characteristics comprises a statistical combination of the first and second characteristics.

34. The method of claim 15, further comprising determining additional characteristics of the wafer using the output, wherein said classifying comprises classifying the wafer based on all of the additional characteristics and the combination of the first and second characteristics.

35. The method of claim 15, further comprising determining additional characteristics of the wafer using the output, wherein said classifying comprises classifying the wafer based on fewer than all of the additional characteristics and the combination of the first and second characteristics.

36. The method of claim 15, wherein the method further comprises classifying the defects based on the first characteristic in an area of the defects.

37. The method of claim 15, wherein the second characteristic further comprises one or more attributes of the defects on the wafer, and wherein the method further comprises classifying the defects based on the first characteristic in an area of the defects in combination with at least one of the one or more attributes of the defects.

38. The method of claim 15, further comprising determining one or more attributes of the first characteristic based on the second characteristic in an area of the first characteristic.

* * * * *